US007473914B2

(12) United States Patent
Todd et al.

(10) Patent No.: US 7,473,914 B2
(45) Date of Patent: Jan. 6, 2009

(54) SYSTEM AND METHOD FOR PRODUCING TERAHERTZ RADIATION

(75) Inventors: Alan M. Todd, Princeton Junction, NJ (US); Hans Peter Bluem, Princeton, NJ (US); Robert Henry Jackson, Jr., Grayson, GA (US)

(73) Assignee: Advanced Energy Systems, Inc., Medford, NY (US)

( * ) Notice: Subject to any disclaimer, the term of this patent is extended or adjusted under 35 U.S.C. 154(b) by 504 days.

(21) Appl. No.: 11/186,429

(22) Filed: Jul. 21, 2005

(65) Prior Publication Data

US 2006/0022151 A1 Feb. 2, 2006

Related U.S. Application Data

(63) Continuation-in-part of application No. 10/903,840, filed on Jul. 30, 2004, now abandoned.

(51) Int. Cl.
*G21G 4/00* (2006.01)
*A61N 5/06* (2006.01)
*G01J 1/00* (2006.01)

(52) U.S. Cl. ............. 250/493.1; 250/495.1; 250/504 R; 315/39.53; 315/39.57; 315/39.77

(58) Field of Classification Search .............. 250/493.1, 250/494.1, 495.1, 503.1, 504 R; 315/39.51, 315/39.53, 39.65, 39.77, 39.75, 39.55, 39.57, 315/39.63
See application file for complete search history.

(56) References Cited

U.S. PATENT DOCUMENTS

| | | | | |
|---|---|---|---|---|
| 4,740,973 | A * | 4/1988 | Madey et al. | 372/2 |
| 4,825,441 | A | 4/1989 | Marshall et al. | |
| 5,363,054 | A | 11/1994 | Bekefi | |
| 5,499,255 | A | 3/1996 | Jackson et al. | |
| 5,663,971 | A | 9/1997 | Carlsten | |
| 5,796,506 | A * | 8/1998 | Tsai | 398/204 |
| 6,014,387 | A | 1/2000 | Carlsten | |
| 6,201,638 | B1 * | 3/2001 | Hall et al. | 359/346 |
| 6,373,194 | B1 * | 4/2002 | Small | 315/39.51 |
| 6,541,785 | B1 * | 4/2003 | Nakasuji | 250/493.1 |
| 6,753,662 | B1 * | 6/2004 | Krafft | 315/505 |
| 6,853,456 | B2 * | 2/2005 | Mells | 356/484 |
| 6,909,104 | B1 * | 6/2005 | Koops et al. | 250/493.1 |

(Continued)

FOREIGN PATENT DOCUMENTS

DE 30 17 125 11/1981

OTHER PUBLICATIONS

Jackson et al., "Development of Compact, Hiogh Power Terahertz Sources", Whitepaper (BMDO) 1998.*

(Continued)

*Primary Examiner*—Bernard E Souw
(74) *Attorney, Agent, or Firm*—Fulbright & Jaworski L.L.P.

(57) ABSTRACT

An apparatus for producing an annular electron beam comprises a cathode for generating electrons, a cavity having an annular shape and operable to receive the electrons, an energy input coupled to the cavity, where the energy input is operable to supply Radio Frequency (RF) energy at the cavity and an energy output coupled to the cavity and operable to receive accelerated electrons from the cavity and operable to output the accelerated electrons as an annular electron beam.

42 Claims, 5 Drawing Sheets

U.S. PATENT DOCUMENTS

| | | | | |
|---|---|---|---|---|
| 6,943,742 | B2 * | 9/2005 | Holly | 343/753 |
| 6,991,927 | B2 * | 1/2006 | Mross et al. | 435/173.1 |
| 7,078,697 | B2 * | 7/2006 | Barker et al. | 250/343 |
| 7,253,426 | B2 * | 8/2007 | Gorrell et al. | 250/200 |
| 2003/0142320 | A1 * | 7/2003 | Mells | 356/484 |
| 2004/0113103 | A1 * | 6/2004 | Zhilkov | 250/504 R |
| 2004/0174521 | A1 * | 9/2004 | Drachev et al. | 356/301 |
| 2006/0022151 | A1 * | 2/2006 | Todd et al. | 250/492.22 |
| 2006/0151722 | A1 * | 7/2006 | Cole et al. | 250/493.1 |
| 2008/0017813 | A1 * | 1/2008 | Vetrovec et al. | 250/504 R |

OTHER PUBLICATIONS

Gellerano et al., "Overview of Terahertz Radiation Sources", Proc. 2004 FEL Conference, pp. 216-221.*

Jackson, R.H. et al, "Design of a far-infrared CHI wiggler free-electron laser", Published by Elsevier Science B.V. (1996) pp. 226-229.

Mallozzi, Jeannette, "Harnessing THz for Medical Applications", R&D Magazine—Oct. 2003, p. 28.

Graydon, Oliver, "Terahertz rays track down drugs", http://optics.org/articles/news/9/10/22/1, Oct. 28, 2003, 2 pages.

Savage, Neil, "Seeing* in a new light", http://www.oemagazine.com/fromTheMagazine/jan03/prodtrends.html, Nov. 25, 2003, 2 pages.

Jackson, Robert et al, "Development of Compact, High Power Terahertz Sources", 9 pages.

Gallerano, G.P. et al, "Overview of Terahertz Radiation Sources", pp. 216-221.

German Office Action issued for related Patent Application No. 10 2005 036 325.3-54, dated Mar. 5, 2008; 7 pages.

* cited by examiner

SYSTEM AND METHOD FOR PRODUCING TERAHERTZ RADIATION

CROSS-REFERENCE TO RELATED APPLICATIONS

This is a continuation-in-part of U.S. patent application, entitled SYSTEM AND METHOD FOR PRODUCING TERAHERTZ RADIATION, and Ser. No. 10/903,840, filed Jul. 30, 2004 by Alan M. Todd, et al.

STATEMENT REGARDING FEDERALLY SPONSORED RESEARCH OR DEVELOPMENT

The subject matter of this application is related to a Small Business Innovation Research project funded by the National Science Foundation under award number 0318910. The government may have certain rights in this invention.

TECHNICAL FIELD

This invention relates generally to the field of terahertz radiation generators and more specifically to a system and method for producing terahertz radiation.

BACKGROUND OF THE INVENTION

Generating Terahertz (THz) radiation in the frequency range from 0.1 to 10 THz is the next frontier in imaging science and technology. THz radiation finds its way into applications ranging from medical imaging, counter terrorism and homeland security, to land mine detection. It is highly desirable to use THz radiation sources for the abovementioned applications because THz radiation is non-ionizing, penetrates plastic, concrete and other common materials and can be used to recognize and identify biological agents and explosives. The wide-range of applications for THz radiation has not been widely developed because there has been a lack of flexible and affordable THz sources or generators. For example, there is an absence of robust THz generators or sources of practical or transportable size.

THz radiation generation has been achieved using several different technologies, none of which presently spans the full range of wavelengths or matches all performance requirements. Techniques for generating THz radiation span a wide range of devices encompassing laser driven semiconductor switches, optically pumped carbon dioxide (FIR) lasers, and electron beam devices, which include mainly backward wave oscillators (BWO) and their variants, Smith-Purcell (grating) devices, gyrotons, conventional free electron lasers (FELs), and synchrotron radiation sources. Most of these devices, however, have been able to generate THz radiation in the power range of only a few milliwatts (mW), more typically 10's of microwatts (μW) with no clear path for scaling to higher power. For many applications, this range of power is insufficient. For example, radar applications, long range secure communications, photon-assisted chemical reactions, certain biomedical applications, and wide field-of-view (FOV) imaging and stand-off detection may require more power.

Increasing peak and average power of THz generation has become more promising with regard to some electron beam devices. Electron beam devices such as FELs and synchrotron radiation sources have demonstrated good potential as high power THz sources. However, these devices have problems with respect to size, cost, and radiation safety. Consequently, known techniques for generating THz radiation are unsatisfactory in certain situations.

BRIEF SUMMARY OF THE INVENTION

The present invention is directed to a system and method for producing an annular electron beam that may be used with a magnetic wiggler to produce high-power THz radiation.

According to one embodiment, an apparatus for producing an annular electron beam is provided. The apparatus for producing an annular electron beam comprises a cathode for generating electrons, a cavity, where the cavity has an annular shape and operable to receive the electrons, an energy input coupled to the cavity, where the energy input is operable to supply Radio Frequency (RF) energy at the cavity and an energy output coupled to the cavity and operable to receive accelerated electrons from the cavity and operable to output the accelerated electrons as an annular electron beam.

According to another embodiment, a method for producing an annular electron beam is provided. The method comprises generating electrons, forming the generated electrons into an annular shape using a cavity, accelerating the electrons through the cavity using a Radio Frequency (RF) energy, and outputting the accelerated electrons as an annular electron beam that is operable to be received by a wiggler.

Some embodiments of the invention may provide one or more technical advantages. One such technical advantage may be a higher average power than known compact THz sources that may thereby enable rapid, wide FOV THz imaging. The term compact refers to the characteristic of having dimensions that make the object capable of being portable so that it may be transported, carried, hauled, packed, shipped or handled by any suitable means. Another technical advantage is that the THz souce may be of practical size and cost, which may result in the proliferation of transportable detection systems. For example, the THz source may be coupled with a detector system, which may be used in the rapid, nondestructive, stand-off detection of hidden weapons, contraband materials, such as plastic explosives, landmines, improvised explosive devices (IEDs) and chemical and biological agents.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

Figure 1:
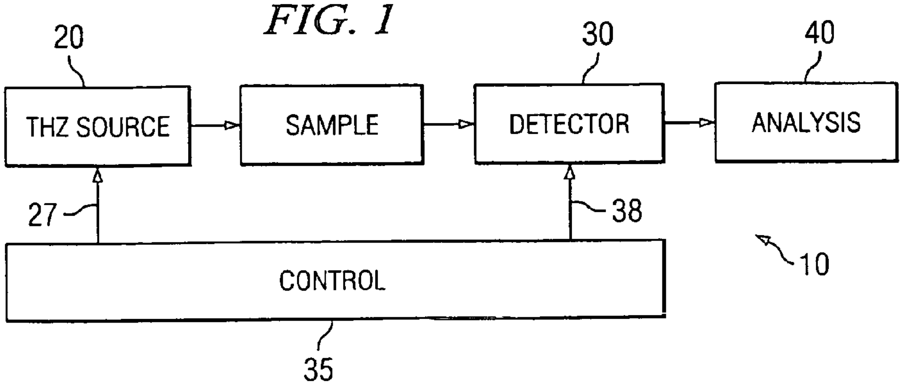
FIG. 1 is a diagram illustrating one embodiment of a Terahertz (THz) radiation detection system using a Terahertz (THz) source in accordance with the present invention.

FIG. 1 is a diagram illustrating one embodiment of a Terahertz (THz) radiation detection system 10 using a Terahertz (THz) source 20 in accordance with the present invention. According to the illustrated embodiment, the THz radiation detection system 10 generates THz radiation using a THz source 20 having a tuning input 27, which item can be used to drive a detector 30 after reflection from or transmission through target object 29, such that an analysis module 40 may perform the analysis desired according to the field of use. For example, system 10 may be used in a wide FOV application where the THz radiation is used as a non-intrusive sensing and non-destructive evaluation system (NDE). In such an application, the THz radiation may be used in the field of stand-off detection where the properties of THz radiation make it possible to identify specific materials such as plastic explosives, and chemical and biological agents.

A compact and high-power THz source 20, as will be described further herein, provides a system 10 suitable for "transportable" commercial applications such as walk-through portals for personnel screening, through-wall imaging for emergency personnel, stand-off explosive detection and crowd screening, and material interrogation, provided the material in question is not contained within metal containers. The dimensions that contribute to the portability of the THz producing system illustrated in FIG. 1 are a diameter in the range of approximately twelve (12) to twenty four (24) inches, and a length in the range of approximately forty (40) inches to sixty (60) inches. The particulars of these dimension will be described more particularly with reference to FIGS. 7A-7B. According to the illustrated embodiment, system 10 comprises THz source 20, detector 30, control module 35, and analysis module 40 coupled as shown in FIG. 1.

THz source 20 produces high-power THz radiation. As used in this document, the term "high power" generally refers to the range of power of at least one Watt, but typically 10's of Watts. For example, the THz radiation may comprise 10, 20, 30 Watts of power, etc., depending on the application. Any other suitable power output of at least one Watt may be produced without departing from the scope of the invention. As was described previously, the THz radiation generated by known THz sources is typically in the range of $10^{-3}$ Watts or less. Those sources include devices, such as conventional FEL devices and those systems based on the production of synchrotron radiation that may be capable of producing THz radiation in the high-power range, however, those prior systems are generally too large and too costly to be found useful in portable applications. As will be described more particularly with reference to FIG. 2, THz source 20 may be configured using a compact coaxial ubitron (a free electron laser or a vacuum electron device capable of producing high power radiation over a broad range of frequencies), for example, that offers both generation of high-power THz radiation and is a portable solution.

Control module 35 provides tuning input 27 that initiates the adjustment of THz source 20 for controlling the THz radiation output. For example, control module 35 may instruct THz source 20 to reduce the output power of the THz radiation by generating an input signal that causes the reduction of the electron beam power to the THz source 20. The adjustment of electron beam power at THz source 20 adjusts the production of output suitable for characteristic signature generation and imaging. According to another embodiment, tuning input 27 comprises a magnetic field adjustment signal that may be used to adjust the output of a magnetic wiggler (or undulator). Tuning input 27 may adjust the THz output power level, the THz output frequency, the THz pulse structure, or it may provide modulation of the THz signal to name just a few possible examples.

Detector 30 receives the THz radiation output from the THz source 20 in order to detect the information related to the THz radiation. According to one embodiment, detector 30 measures the electric field associated with the generated THz radiation. Typically, the electric field can be detected to further analyze the absorption of the THz pulse and the phase delays that detector 30 receives as the THz radiation propagates through the sample comprising materials of varying refractive index. Detector 30 generates a detection signal that analysis module 40 uses to analyze the THz radiation information in order to generate analysis reports. Other detection schemes are also possible covering, among other applications, spectral analysis or imaging.

Control module 35 generates a control signal 38 that controls operation of detector 30. In one embodiment, control module 35 comprises software and hardware that control the analysis of the information related to the THz radiation detected by detector 30. In another embodiment, control module 35 may comprise software and hardware that control how detector 30 measures the electric field associated with the generated THz radiation. For example, control module 35 may be used to instruct detector 30 to ignore certain wavelengths associated with specific materials, such that detector 30 may detect the specific spectrography desired. In particular, if system 10 is used in the field of land mine detection, control module 35 may be configured to instruct detector 30 to detect those wavelengths associated with the materials sought to be detected. In another embodiment, control module 35 may be used to instruct the detector in the generation of an image of the area of interest.

Analysis module 40 has software and hardware that analyzes the information related to the THz radiation. The software and hardware may be used to compare the detected spectrum from a library of spectra. Or, if used as an imaging device, the software and hardware may be used to analyze the image in comparison to items of interest.

Figure 2:
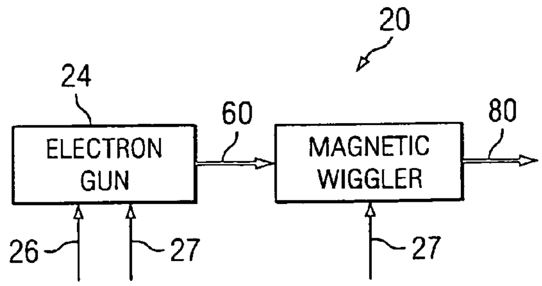
FIG. 2 is a diagram illustrating one embodiment of a THz source that may be used with the system of FIG. 1.

FIG. 2 is a diagram illustrating one embodiment of a THz source 20 that may be used with system 10 of FIG. 1. According to the illustrated embodiment, THz source 20 includes an electron gun 24 and a magnetic wiggler 28 coupled as shown in FIG. 2. In one embodiment, electron gun 24 comprises an RF gun, which produces an annular electron beam. Electron gun 24 may comprise a Radio Frequency (RF) electron gun, a thermionic RF electron gun, an RF field emission electron gun, or an RF photocathode gun. A gated or pulsed DC electron gun may also be used as electron gun 24 without departing from the scope of the invention. Any other suitable device operable to produce an annular electron beam 60 may be used as electron gun 24 without departing from the scope of the invention.

Electron gun 24 produces and accelerates annular electron beam 60 that is injected into a magnetic field generated by magnetic wiggler 28. The annular electron beam 60, comprising an annular shape rather than a pencil beam shape, leads to reduced space-charge effects. According to one embodiment, the annular RF electron beam 60 is introduced into a coaxial structure coupled with magnetic wiggler 28 to drive the $TE_{01}$ coaxial waveguide mode of the device. Annular electron beam 60 coupled with magnetic wiggler 28 drives the $TE_{01}$ coaxial waveguide mode to allow for higher power operation. The $TE_{01}$ coaxial waveguide mode has a vanishing electric field at the surface of the conductors, thus reducing the potential for electric field breakdown. By combining an electron gun 24 that introduces an annular electron beam 60 into magnetic wiggler 28 for coupling to the $TE_{01}$ coaxial waveguide mode in a waveguide cavity, THz source 20 may be described as a "closed" radiation system.

Magnetic wiggler 28 is a device that is configured to produce a wiggler field that performs as a magnetic well which receives annular electron beam 60 to allow coupling to the $TE_{01}$ coaxial waveguide mode in order to produce high-power THz radiation 80. The configuration of one embodiment of magnetic wiggler 28 will be more particularly described with reference to FIG. 6. According to one embodiment a coaxial hybrid iron (CHI) wiggler may be used as magnetic wiggler 28. Any other suitable device for producing a wiggler field may be used without departing from the invention. Magnetic wiggler 28 may include a tuning input 22 for adjusting its magnetic field. The adjustment of the magnetic field may be performed in addition to adjusting the RF input of electron gun 24.

Although THz source 20 has been described as an apparatus that operates generally as an oscillator, other suitable configurations may be used. According to the illustrated embodiment, mode selection 26 is a design parameter that defines whether THz source 20 operates in an amplifier mode or an oscillator mode. These modes of operation will be more particularly described with reference to FIGS. 3 and 4. THz source 20 may be modified without departing from the scope of the invention. An example of THz source 20 operating as an amplifier source will be described with reference to FIG. 3.

Figure 3:
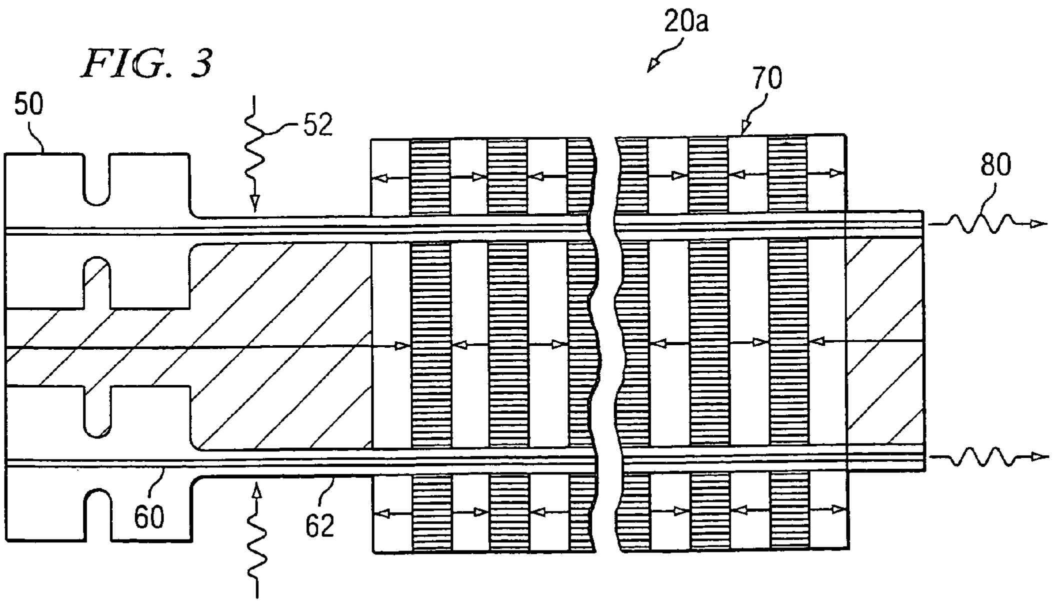
FIG. 3 is a diagram illustrating an example of an embodiment of the THz source operating in the amplifier mode shown in FIG. 3.

FIG. 3 is a diagram illustrating an example of an embodiment of THz source 20*a* operating in the amplifier mode shown in FIG. 3. According to the illustrated embodiment, electron gun 50 introduces annular electron beam 60 to a coaxial transmission line 62 so that magnetic wiggler 70 may undulate annular electron beam 60 through a wiggler field. The coaxial transmission line 62 comprises an inner conductor where permanent magnets are placed in an alternating configuration, perhaps but not necessarily spaced by soft magnetic material such as iron. A similar alternating magnet configuration is also mounted outside the outer conductor, with the outer permanent magnets longitudinally offset from the inner magnets by 180 degrees, thereby forming the wiggler field. The annular electron beam 60 is produced from an annular cathode at electron gun 50. The THz seed signal 52 is introduced into the coaxial transmission line 62 just prior to the interaction region of magnetic wiggler 70, where the spatially modulated electron beam interacts with the $TE_{01}$ coaxial waveguide mode and produces an amplified THz signal 80. As was previously described, operation in a coaxial $TE_{01}$, mode allows for higher power operation.

In this embodiment, the configuration shown is an amplifier operation mode, which requires feeding a seed THz signal 52 into the interaction region. Seed THz signal 52 may be produced using a standard semiconductor THz emitter. This amplifier operation mode, however, introduces some complication and cost. A regenerative amplifier configuration or an oscillator operation mode may be used to potentially reduce the complication of the design and reduce cost. In order to form an oscillator cavity, one may cause the inlet to and the outlet from the interaction region cavity neck to partially reflect the THz radiation. At the electron beam inlet, one would desire near total reflection of the trapped THz radiation. At the output end, a partial reflector would be used in order to allow a portion of the THz radiation to exit the device.

Although a magnetic wiggler 70 having a permanent magnet configuration has been described, other suitable wiggler structures and configurations may be used as magnetic wiggler 70 without departing from the scope of the invention. One such suitable wiggler that may be used is the coaxial hybrid iron (CHI) wiggler, described with more particularity in FIG. 6 and by U.S. Pat. No. 5,499,255, issued to Jackson et al., titled "Coaxial Hybrid Wiggler."

Figure 6:
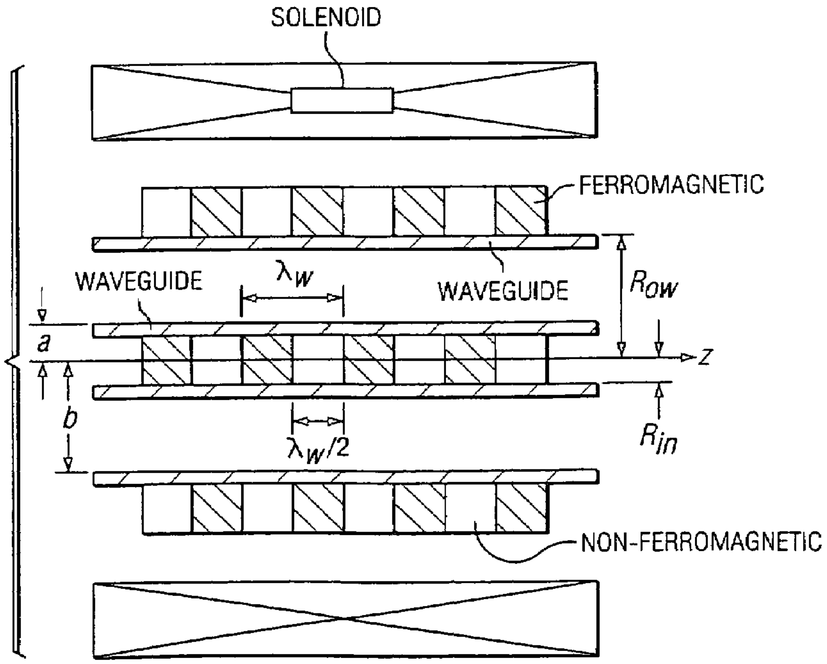
FIG. 6 is a diagram illustrating an example of an embodiment of a coaxial hybrid (CHI) wiggler that may be used with the THz source of FIGS. 1-3.

FIG. 6 is a diagram illustrating an example of an embodiment of a coaxial hybrid (CHI) wiggler that may be used with the THz source of FIGS. 1-3. The CHI wiggler has inner and outer coaxial iron pole pieces, shifted relative to each other by one half period. The pole pieces are also immersed in a strong solenoidal magnetic field. The iron causes ripples in the magnetic flux lines resulting in a periodic radial magnetic field, Br. The iron disks in the inner coax member enhance the ripples, almost doubling the magnitude of the radial magnetic field. The radial field increases with applied solenoidal field until saturation occurs in the iron.

Referring now to FIG. 3, with respect to other design parameters of THz source 20*a*, it is important to appreciate that the output frequency of the radiation depends on the square of the electron beam voltage and the inverse of the magnetic wiggler period. Thus, the electron beam voltage must be sufficiently high to permit a practical magnet spacing at magnetic wiggler 70. The minimum beam voltages necessary to generate 1 THz radiation ($\lambda$~300 $\mu$m) for wiggler periods of 3, 1, and 0.5 cm are 3.1, 1.6, and 0.96 mega electron volt (MeV) respectively. However, if the wiggler period is shortened for a fixed geometry, the field amplitude drops dramatically and the gain of the device is reduced. In one embodiment, electron gun 50 comprising a gated or pulsed DC electron gun would probably not be operated above approximately one (1) MeV. Additionally, one would probably not use wiggler periods shorter than about 0.5 cm because these parameters appear impractical from a performance and fabrication perspective. In other embodiments, RF electron gun 50 delivers an electron beam from approximately one to three MeV into a magnetic wiggler 70 having a wiggler period of approximately one (1) cm. The configuration of THz source 20*b* may be modified without departing from the scope of the invention. For example, an electron gun 50 comprising a field emission gun may be used.

Figure 4:
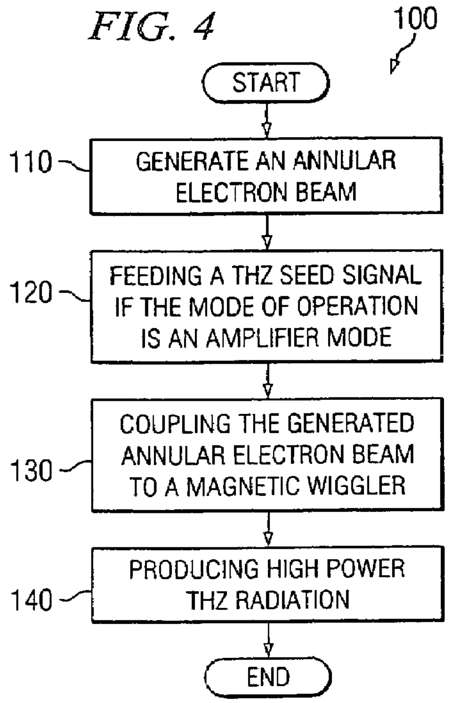
FIG. 4 is a an operational flowchart of one embodiment of a method for generating THz radiation in accordance with the present invention.

FIG. 4 is an operational flowchart of one embodiment of a method 100 for generating THz radiation 80 in accordance with the present invention. The method begins at step 110 where an electron gun 24 generates an annular electron beam 60. According to one embodiment electron gun 24 comprises a thermionic RF gun that generates a relativistic annular electron beam, where the electrons comprising the beam reach a velocity that is independent of their respective energy levels so that electrons of different levels can maintain their velocity through acceleration while maintaining a proper phase relative to an RF field. At step 120 a THz seed signal 52 is fed to the interaction region of THz source 20 if the mode of operation is an amplifier mode. This step would be omitted if THz source 20 operates as an oscillator.

The method proceeds to step 130 where a magnetic wiggler 28 is coupled to the generated annular electron beam 60. In some embodiments, magnetic wiggler 28 comprises a permanent magnet device, while in other embodiments, magnetic wiggler 28 comprises a CHI wiggler device. A high-power THz radiation 80 is produced at step 140. As was previously described, a high power THz signal is defined in this document as one that comprises power greater than one Watt, but generally greater than 10 Watts.

Figure 5:
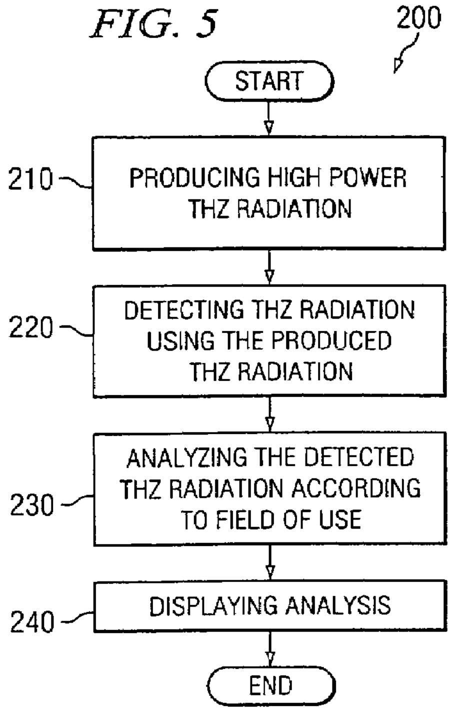
FIG. 5 is an operational flowchart of one embodiment of a method for using the THz source of FIG. 2 with the THz radiation detection system of FIG. 1.

FIG. 5 is an operational flowchart of one embodiment of a method 200 for using the THz source 20 of FIG. 2 with the THz radiation detection system 10 of FIG. 1. The method begins at step 210 where a THz source 20 produces high-power THz radiation 80. At step 220 detector 30 detects THz radiation using the produced THz radiation 80. For example, detector 30 detects the electrical field associated with the THz radiation 80 in order to obtain the information corresponding to the THz radiation. For certain applications, detector 30 may have to be synchronized with the production of THz radiation from THz source 20. At step 230, analysis module 40 analyzes the information determined by detector 30 in order to provide reports according to the field of use. For example, in the field of use of medical imaging, the information determined by detector 30 may comprise information related to biological matter which analysis module 40 analyses to obtain an image corresponding to the biological matter being imaged. Accordingly, the method terminates after displaying the analysis at step 240. Although an example of medical imaging has been described as a field of use for the invention, such field of use may include many other applications that would benefit from transportable, high-power THz radiation systems.

Figure 7A:
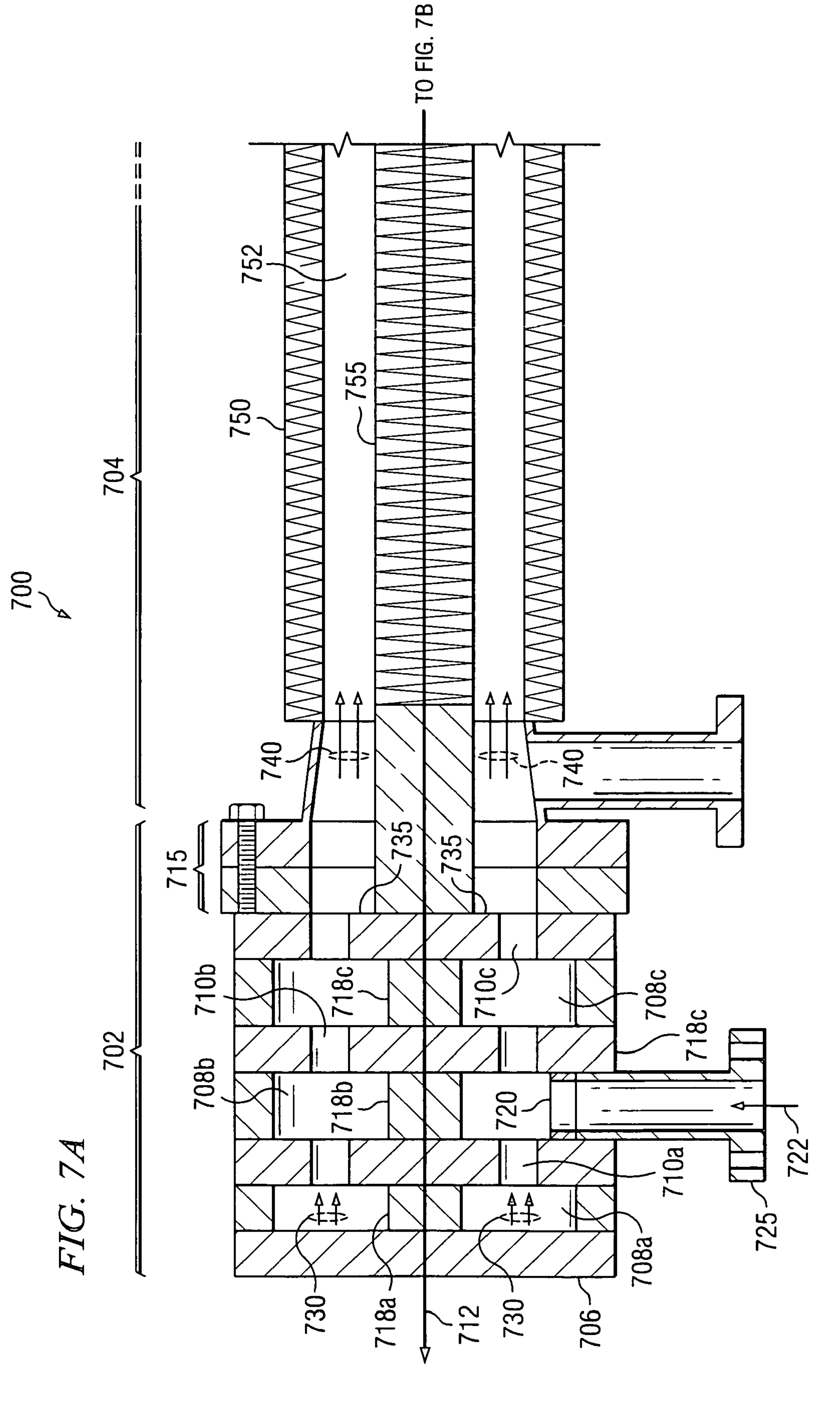
FIG. 7 is a diagram illustrating an example of an embodiment of a THz source that may be used with the system of FIG. 1.
Figure 7B:
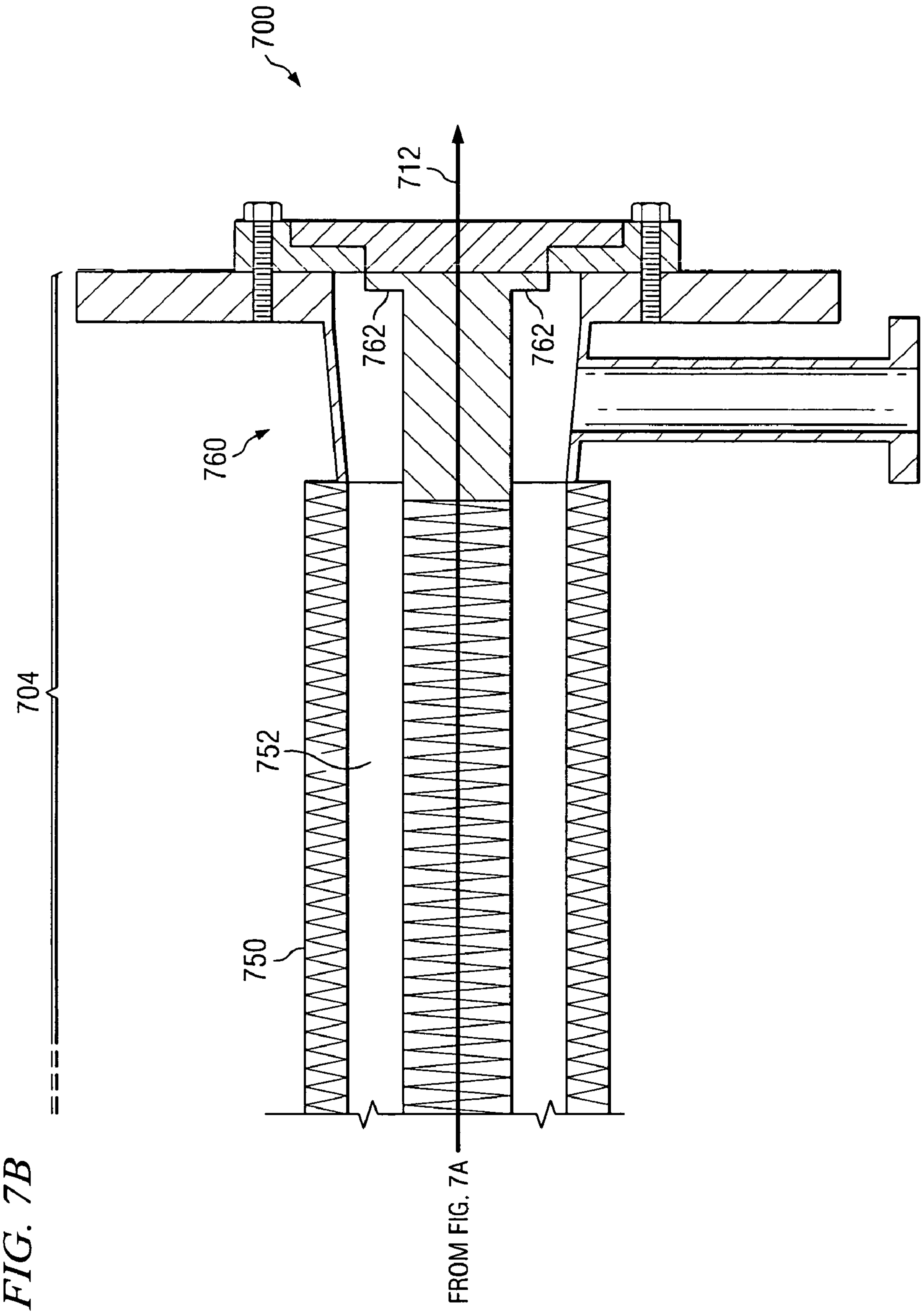

FIGS. 7A-7B illustrate another example of an embodiment of THz source 700. In general, THz source 700 includes a first section 702 and a second section 704 coupled together as shown in FIG. 7A. First section 702 generates an electron beam 740 in the form of an annular beam that is accelerated using at least one accelerating cell 708. According to the illustrated embodiment, accelerating cell 708 comprises an annular cavity suitable for holding electrons while an electric field causes the electrons to be accelerated. Other suitable structures may be used as accelerating cells 708 without departing from the scope of the invention. The first section may also include a coupling iris 710 for coupling adjacent accelerating cells 708 and other interfaces, such as interface 715. For example, the embodiment shown in FIG. 7A comprises three accelerating cells 708*a-c*, and three coupling irises 710*a-c*. More or fewer coupling irises 710, and more or fewer accelerating cells 708 may be used without departing from the scope of the invention. According to the illustrated embodiment, coupling irises 710 comprise a pass-through opening of a reduced area as compared to the adjacent cavities. The opening may comprise any shape and dimension suitable for passing through electrons from one adjacent cavity to another. Any other suitable structure may be used as coupling irises 710 without departing from the scope of the invention.

The first section 702 comprises a first acceleration wall 706, accelerating cells 708, coupling irises 710, and an interface 715. The first acceleration wall 706 includes a cathode for producing electrons 730. The cathode may be any suitable device for producing electrons 730, such as a thermionic cathode, field emission cathode, or photo-emission cathode. An embodiment of a cathode for producing electrons 730 will be more particularly described with reference to FIG. 8.

Electrons 730 are accelerated at accelerating cell 708*a* designed such that an off-axis, coaxially uniform accelerating field is produced at accelerating cell 708*a*. An accelerating cell 708 may be coupled to a waveguide port 720 for introducing an RF input 722 to the accelerating cell 708. Other types of RF input may be used at accelerating cells 708. For example, a coaxial transmission line may be used without departing from the scope of the invention.

Accelerating cells 708*a-c* are aligned along an axis 712 of THz source 700. That is, in the present embodiment, an accelerating cell 708 is cylindrically symmetric and may contain a uniform coaxial cavity, where the center of the coaxial cavity is aligned with axis 712. Along axis 712, center portions 718*a-c* are substantially aligned to form a central coaxial support that is coupled to the second portion 704 through interface 715. Accelerating cells 708 each form a cavity resonator of any suitable configuration, such as the shown cross-sectional configuration, foreshortened coaxial line resonator configuration, foreshortened radial line resonator configuration, conical line resonator configuration, folded coaxial line resonator configuration, or other suitable cavity resonator configuration.

In the present embodiment, three (3) accelerating cells 708*a-c* are shown. The accelerating cells 708*a-c* are coupled through coupling irises 710*a-c*. Although three accelerating cells 708 are shown, first section 702 may comprise any suitable number of accelerating cells 708 and each accelerating cell 708 may be configured and powered independently from each other. For example, accelerating cell 708*a* may be configured differently than accelerating cells 708*b* and 708*c*. Additionally, although a waveguide port 720 is shown coupled to accelerating cell 708*b*, a waveguide port 720 may be coupled to any accelerating cell 708. As an alternative embodiment, each accelerating cell 708 may be coupled to a waveguide port 722, such that each accelerating cell 708 may be driven using different fields, without departing from the scope of the invention.

In other embodiments, each accelerating cell 708 may operate independently from each other and with little to no coupling of the accelerating field. For example, accelerating cell 708*a* may be driven using an RF input 722 through a waveguide port 720 without coupling to adjacent accelerating cell 708*b*, which would have its own RF input 722. That is, in this alternative embodiment, accelerating cells 708*a* and 708*b* would be individually driven, such that coupling of the accelerating field through iris 710*a* is avoided. This configuration may result in a separate waveguide 725 to each cavity, or a series of nested coaxial transmission lines. A separate waveguide port 720 may be used to drive each individual accelerating cell 708 as has been previously described.

In the illustrated embodiment, first section 702 comprises a gun assembly that operates in a specific mode according to its design. The mode of the gun assembly illustrated in the embodiments shown in FIGS. 7A-7B results in the peak in the accelerating field that is formed at each accelerating cell 708 and the null in the radial electric field to occur off-axis. The accelerating field may be referred to as standing wave electric fields that are formed by injecting the RF input 722 to the accelerating cell 708*b*. While the cathode is generating electrons 730 to a first accelerating cell 708*a*, the standing wave energy at that first accelerating cell 708*a* produces an axial electric field of sufficient strength to pull the electrons 730 away from first accelerating wall 706. The electrons are also accelerated through the first coupling iris 710*a*. Coupling irises 710 are the boundaries of the openings of the accelerating cells 708 and are equipped with at least one orifice to allow a beam of electrons 730 to pass through adjacent accelerating cells 708. This pattern of acceleration is continued through each of the accelerating cells 708 to form an annular beam 740 having a suitable amount of energy. Accelerating cells may be added or omitted, together with coupling irises, to achieve an annular beam 740 having a particular level of energy.

Configuring the accelerating cells 708 and RF input(s) 722 to accelerate electrons 730 and using coupling irises 710 to guide the accelerated electrons through the cavities of accelerating cells 708 may result in various advantages. An advantage is a THz source assembly that has a cylindrically symmetric design that may be configured in modules to achieve a particular energy level and to provide a desired field pattern. Also, the ability to inject varying levels of RF input 722 at any or all of the cavities of accelerating cells 708 may result in the advantage of dynamic adjustment of control and input, which may result in increase control and accuracy. As was previously discussed, the off-axis peak in the accelerating field and the null in the radial electric field are close in proximity, which may provide an advantage of a THz source that produces a high quality annular beam 740, or other off-axis electron beams. The term "off-axis" is used in this document to refer to the fact that the electron beams produced are not pencil beams or what is traditionally understood as being collimated beams. Although a symmetrically cylindrical annular beam 740 is described, it is not necessary that annular beam 740 be symmetrical. Annular beam 740 may have any shape, configuration, energy level, or intensity, so long as its substantial radiating portions are not propagated along a central line or axis, such as axis 712.

First section 702 is coupled to a second section 704 using an interface 715, which is aligned along axis 712. This coupling enables the propagation of annular beam 740 through a wiggler 750, thereby generating high power THz radiation. As is known in the art, a wiggler 750, such as the magnetic wiggler configuration described with reference to FIG. 6, is used to provide variations in the radial magnetic field, which produce variations in the electron beam transverse motion enabling the passing annular beam 740 to produce THZ radiation.

Another advantage of the design of the embodiment shown in FIGS. 7A-7B is the alignment of the center structures of the first portion and the center conductor 755 of the wiggler 750. This architecture provides an on-axis support structure, such as along axis 712, that can be accomplished using any suitable material, such as conducting material, or a dielectric material. This architecture also provides the advantage that the on-axis support provides support for the center conductor 755 of the downstream coaxial structure that forms wiggler 750.

Annular beam 740 is accelerated using a substantially symmetrical RF field at an off-axis location. Although typically Direct Current (DC) guns have been used to produce and accelerate annular electron beams, to produce high-energy annular electron beams using DC guns has typically required high DC voltages. A high-energy annular electron beam comprises an energy level of at least 500 keV. The embodiments described with respect to FIG. 7 are generally directed to configuration of a gun assembly that uses RF to produce a high-energy annular beam while using less than 200 kiloVolts (kV) of DC voltage. An RF gun having some or all of the design parameters herein described may produce high energy beams, of at least 500 keV, with lower DC voltages, less than 100 kV, than those traditionally used with respect to DC guns, which would require up to 1.5 to 2 MV to operate at the full election beam voltage.

Referring now to FIG. 7B second section 704 includes wiggler 750, which has a center conductor 755 that is aligned with axis 712. Annular beam 740 enters the wiggler cylindrical coaxial structure 752, which has a downstream end 760 that steers the annular beam 740 using a prescribed field pattern. The downstream end 760 includes a reflective wall 762 that reflects a portion of the THz radiation that does not radiate out of the apparatus. Reflective wall 762 may comprise either a fully reflective surface, such as a mirror, or a partially reflective surface. The reflected radiation may be controlled to substantially prevent it from entering the first portion 702. For this purpose, a reflective wall 735, shown in FIG. 7A, may be used. Reflective wall 735 may also be either a fully reflective surface or a partially reflective surface.

Turning back to FIG. 7A, first section 702 may comprise dimensions that contribute to the portability characteristics of the THz system described with reference to FIG. 1. According to one embodiment, first section 702 comprises a length in a range of approximately seven (7) to ten (10) inches. This length may be increased or decreased depending on various factors, one of which is the number of accelerating cells 708 and coupling irises 710 used. Other factors may include the thickness of first accelerating wall 706, addition of walls, reduction of cavities, and other suitable modifications. With regard to a diameter, first section 702 may comprise a diameter in a range of approximately ten (10) to twenty (20) inches. Other suitable dimensions may be used without departing from the scope of the invention. Second section 704 may also comprise dimensions that contribute to the portability characteristics of the THz system described with reference to FIG. 1. In this embodiment, section 704 has a length in a range of approximately forty (40) inches to fifty (50) inches. This length may be increased or decreased depending on its configuration without departing from the scope of the invention.

Figure 8:
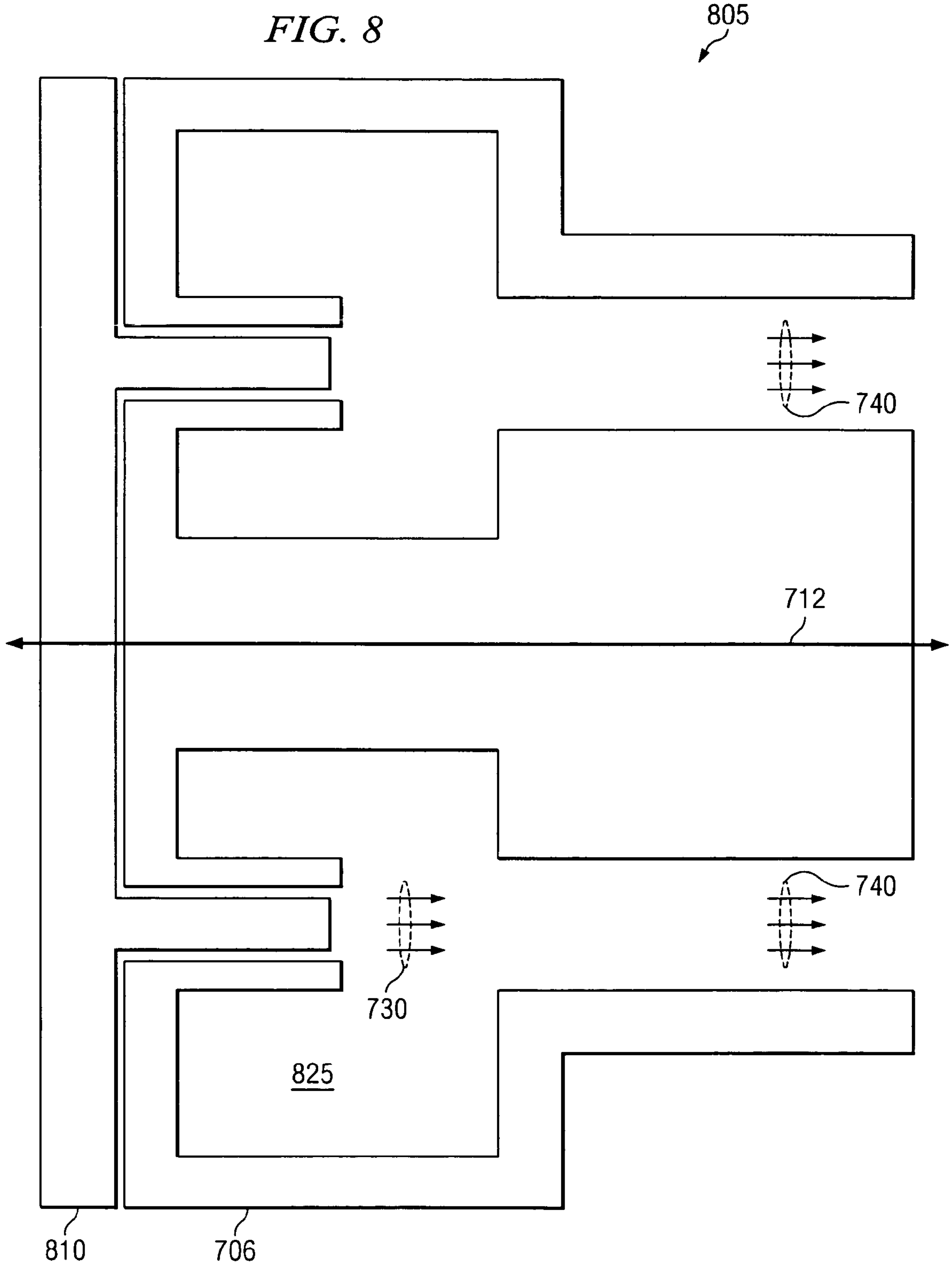
FIG. 8 is a diagram illustrating an example of a cathode that may be used with an embodiment of a THz source.

Turning now to FIG. 8, a first acceleration wall 706 comprises a cathode 810 and is integrated into a first module 805 of first portion 702. In the illustrated embodiment, cathode 810 comprises an annular shape and portions of cathode 810 protrude in the cavity of a cathode cavity 825. The architecture of cathode 810 may be such that an annular ring made of continuous material may be used. Other configurations may be used, such as individual pieces of arbitrary shape that are arranged in a ring pattern or concentric design, without departing from the scope of the invention. The electron generating element of cathode 810 may be located at any appropriate radius from the central axis 712. The placement of cathode 810 with respect to axis 712 is such that the radius of cathode 810 is located at the position of a uniform accelerating field. Other positions for cathode 810 may be used without departing from the scope of the invention.

In another embodiment of first module 805, the cathode cavity 825 associated with cathode 810 would operate at a harmonic of the fundamental gun frequency. For example, if the gun assembly was operated at a specific fundamental frequency, the cathode cavity 825 may be operated at a harmonic of that specific fundamental frequency. In this embodiment, a short cathode cavity, operating at a harmonic of the fundamental gun frequency, may be used for the gated production of electrons 730. The harmonic frequency is suitably phased with respect to the fundamental gun accelerating frequency to produce the above-mentioned gated electron production. This phase may be also described as a timing parameter for determining the times at which the electron beam is generated and the timing of the accelerating fields in the accelerating cavities 708 (shown with respect to FIG. 7). Furthermore, this cathode cavity operating at a harmonic of the other gun cavities could be designed such that a portion of the fundamental frequency power in the subsequent accelerating cavity can couple into the harmonic cavity and superimpose upon the harmonic frequency signal, thus creating a combined signal of a shape to better extract properly timed electron bunches.

As was also previously described, cathode 810 may be of any suitable device for producing electrons 730. However, some devices may be more suitable for producing electrons 730 in the gating design just described. For instance, a thermionic or field emission cathode may be more useful in the configuration that allows for the gated electron production. Other cathode types, such as a photo-emission cathode, may be used depending on the laser characteristics. Additionally, a solenoid may be included at first module 805 to generate a static magnetic field in order to control annular electron beam 740. This solenoid may be used to maintain a substantially uniform static magnetic field from cathode 810 to the interface 715 (shown at FIG. 7).

Although the present invention and its advantages have been described in detail, it should be understood that various changes, substitutions and alterations can be made herein without departing from the invention as defined by the appended claims. Moreover, the scope of the present application is not intended to be limited to the particular embodiments described in the specification. As one will readily appreciate from the disclosure, other embodiments that perform substantially the same function or achieve substantially the same result as the corresponding embodiments described herein may be utilized. Accordingly, the appended claims are intended to include within their scope such embodiments.

What is claimed is:

1. An apparatus for producing an annular electron beam in a THz radiation application comprising:

a cathode for generating electrons, a cavity, the cavity having an annular shape and operable to receive the electrons;

an energy input coupled to the cavity, where the energy input is operable to supply Radio Frequency (RF) energy at the cavity; and an energy output coupled to the cavity and operable to receive accelerated electrons from the cavity and operable to output the accelerated electrons as an annular electron beam, wherein the cavity comprises a first cavity and a second cavity, and wherein the energy input comprises a first energy input and a second energy input, the first energy input supplying a first Radio Frequency (RF) energy to the first cavity, and the second energy input supplying a second RF energy to the second cavity.

2. The apparatus of claim 1, wherein the first cavity is located adjacent to the cathode and operable to receive electrons from said cathode, and where the second cavity is coupled to the first cavity via a coupling iris.

3. The apparatus of claim 1, further comprising a waveguide port for supplying the RF energy to the cavity.

4. The apparatus of claim 1, wherein the first cavity and the second cavity are substantially aligned along a central axis.

5. An apparatus for producing an annular electron beam in a THz radiation application comprising:

a cathode for generating electrons, a cavity, the cavity having an annular shape and operable to receive the electrons;

an energy input coupled to the cavity, where the energy input is operable to supply Radio Frequency (RF) energy at the cavity; and an energy output coupled to the cavity and operable to receive accelerated electrons from the cavity and operable to output the accelerated electrons as an annular electron beam, wherein the cavity comprises a first cavity and a second cavity, and wherein the energy input comprises a first energy input and a second energy input, the first energy input supplying a first Radio Frequency (RF) energy to the first cavity and the second energy input supply ring a second Radio Frequency (RF) energy to the second cavity; and where each energy input comprises a phase and a power level that is independently adjusted to provide control of energy spread and bunch length associated with the annular electron beam.

6. The apparatus of claim 5, wherein the apparatus further comprises a wiggler that receives the annular electron beam, and where the bunch length is sufficiently short to produce a coherent spontaneous radiation at the wiggler.

7. The apparatus of claim 5, wherein the first RF energy has a first frequency and wherein the second RF energy has a second frequency, where the first frequency and the second frequency are substantially the same.

8. The apparatus of claim 1, wherein the annular shape comprises a center that is substantially aligned a long a central axis, and wherein the RF energy forms an accelerating field and an electric field at the cavity, and where the peak of the accelerating field and the null of the electric field occur at a distance from the central axis.

9. The apparatus of claim 1, wherein the supply of RF energy is performed using less than 200 kiloVolts (kV) of Direct Current (DC) voltage.

10. The apparatus of claim 1, further comprising a wiggler and an interface for coupling the annular beam to the wiggler.

11. The apparatus of claim 10, wherein the interface comprises a totally reflective surface to substantially prevent reflected energy from entering the cavity.

12. The apparatus of claim 1, wherein the cathode is one type of cathode selected from the group comprising: a thermionic cathode, a field emission cathode, and a photo-emission cathode.

13. The apparatus of claim 1, wherein the cavity has one configuration prom the group of configurations comprising: foreshortened coaxial line resonator configuration, foreshortened radial line resonator configuration, conical line resonator configuration, and folded coaxial line resonator configuration.

14. A method for producing an annular electron beam in a THz radiation application comprising:

generating electrons;

forming the generated electrons into an annular beam shape using a cavity;

accelerating the electrons through the cavity using a Radio Frequency (RF) energy; and outputting the accelerated electrons as an annular electron beam that is operable to be received by a wiggler, wherein the cavity comprises a first cavity and a second cavity, and wherein an energy input to the cavity comprises a first energy input and a second energy input, the first energy input supplying a first Radio Frequency (RF) energy to the first cavity, and the second energy input supplying a second RF energy to the second cavity.

15. The method of claim 14, further comprising injecting into the cavity the RF energy through a waveguide port.

16. The method of claim 14, wherein the step of accelerating the electrons further comprises accelerating the electrons from the first cavity to the second cavity via a coupling iris.

17. A method for producing an annular electron beam in a THz radiation application comprising:

generating electrons:

forming the generated electrons into an annular beam shape using a cavity;

accelerating the electrons through the cavity using a Radio Frequency (RF) energy; and outputting the accelerated electrons as an annular electron beam that is operable to be received by a wiggler, wherein the cavity comprises a first cavity and a second cavity, and where the step of accelerating the electrons further comprises accelerating the electrons from a first cavity to a second cavity via a coupling iris, wherein the method further comprises inputting into the first cavity a first RF energy and into the second cavity a second RF energy, where the first RF energy comprises a first frequency and the second RF energy comprises a second frequency, and where the first frequency is different from the second frequency.

18. A method for producing an annular electron beam in a THz radiation application comprising:

generating electrons;

forming the generated electrons into an annular beam shape using a cavity;

accelerating the electrons through the cavity using a Radio Frequency (RF) energy; and outputting the accelerated electrons as an annular electron beam that is operable to be received by a wiggler, the method further comprising gating the production of electrons by phasing the production of electrons according to a timing associated with the generation of the electrons generated and the timing of the electric field formed at the cavity.

19. The method claim 14, wherein the annular electron beam comprises an energy level of at least 500 keV.

20. The method of claim 14, further comprising interfacing the annular electron beam to a wiggler for producing a high-energy annular beam.

21. An apparatus for generating a high-energy annular electron beam for use in a THz radiation application comprising:

means for generating electrons;

means for forming the generated electrons into an annular shape, where the means for forming the generated electrons is coupled to the means for generating electrons;

means for accelerating the electrons through the means for forming the generated electrons; and means for delivering the accelerated electrons as an annular electron beam, where the annular electron beam comprises an energy level of at least 500 keV, wherein the forming means includes a cavity that comprises a first cavity and a second cavity, and wherein an energy input to the cavity comprises a first energy input and a second energy input, the first energy input supplying a first Radio Frequency (RF) energy to the first cavity, and the second energy input supplying a second RF energy to the second cavity.

22. A system for producing THz radiation, comprising;

an electron source comprising;

an annular cathode for generating an annular electron beam, a cavity having an annular shape and operable to receive the electrons, and an energy input coupled to the cavity, where the energy input is operable to supply Radio Frequency (RF) energy at the cavity, and an energy output coupled to the cavity and operable to receive accelerated electrons from the cavity and operable to output the accelerated electrons as an annular electron beam; and a wiggler coupled with the electron source for undulating the electron beam and for coupling the electron beam to a coaxial waveguide mode and for producing THz radiation having a high average power, wherein the cavity comprises a first cavity and a second cavity, and wherein the energy input comprises a first energy input and a second energy input, the first energy input supplying a first Radio Frequency (RF) energy to the first cavity, and the second energy input supplying a second RF energy to the second cavity.

23. The system of claim 22, wherein the high average power comprises power of at least one Watt.

24. The system of claim 22 comprising a length in the range of approximately sixty inches and comprising a diameter of approximately twelve inches.

25. The system of claim 22 comprising dimensions that make the system compact.

26. A system for producing THz radiation, comprising:

an electron gun having a coaxial structure and comprising an annular cathode for generating an annular electron beam; and a magnetic wiggler coaxially coupled with the electron gun for undulating the electron beam and for coupling The electron beam to a coaxial waveguide mode and for producing THz radiation having a high average power, wherein the annular cathode includes a cavity that comprises a first cavity and a second cavity, and wherein an energy input to the cavity comprises a first energy input and a second energy input, the first energy input supplying a first Radio Frequency (RF) energy to the first cavity, and the second energy input supplying a second RF energy to the second cavity.

27. The system of claim 26, wherein the high average power comprises power of at least one Watt.

28. The system of claim 26, further comprising a coaxial transmission line for coupling the electron gun and the magnetic wiggler.

29. The system of claim 26, further comprising a tunable input for adjusting the magnetic field of the magnetic wiggler and for adjusting the electron beam output voltage of the electron gun for adjusting a THz output frequency.

30. The system of claim 26, wherein the system is further operable to receive a THZ seed signal that is amplified within a magnetic wiggler region of the magnetic wiggler.

31. The system of claim 26, the electron gun comprising one of a gated Direct Current (DC) electron gun, a Radio Frequency (RF) thermionic electron gun, an RF field emission electron gun, and an RF photocathode gun.

32. The system of claim 31, wherein the electron gun and the magnetic wiggler are coupled together to operate in an oscillator mode.

33. The system of claim 26, wherein the magnetic wiggler comprises a permanent magnet wiggler.

34. The system of claim 26, wherein the magnetic wiggler comprises a Coaxial Hybrid (CHI) wiggler.

35. A method of producing Terahertz radiation comprising:

generating an annular electron beam by an electron gun having a coaxial structure and comprising an annular cathode;

coaxially coupling the generated annular electron beam to a magnetic wiggler; and producing high power THz radiation, wherein the annular cathode includes a cavity that comprises a first cavity and a second cavity, and wherein an energy input to the cavity comprises a first energy input and a second energy input, the first energy input supplying a first Radio Frequency (RF) energy to the first cavity, and the second energy input supplying a second RF energy to the second cavity.

36. The method of claim 35, wherein the high power THz radiation comprises power of at least one Watt.

37. The method of claim 35, wherein coupling the generated annular electron beam to a magnetic wiggler is performed using a coaxial transmission line driven in $TE_{01}$ coaxial waveguide mode.

38. The method of claim 35, further comprising receiving a tunable input that adjusts the magnetic field of the magnetic wiggler.

39. The method of claim 38, wherein the tunable input is further operable to adjust the electron beam of the electron gun.

40. The method of claim 35, further comprising establishing an operation mode associated with the electron gun and the magnetic wiggler are coupled.

41. The method of claim 40, wherein the operation mode comprises one of an amplifier mode and an oscillator mode.

42. A system for producing Terahertz (THz) radiation comprising:

an annular electron beam producing means having a coaxial structure and for generating a THz signal; and a wiggler field producing means for coaxially coupling the electron beam to a coaxial waveguide mode, where the electron beam producing means and the wiggler field producing means are operable to produce THz radiation having high average power, wherein the annular cathode includes a cavity that comprises a first cavity and a second cavity, and wherein an energy input to the cavity comprises a first energy input supplying a first Radio Frequency (RF) energy to the first cavity, and the second energy input supplying a second RF energy to the second cavity.

* * * * *

UNITED STATES PATENT AND TRADEMARK OFFICE
CERTIFICATE OF CORRECTION

PATENT NO. : 7,473,914 B2
APPLICATION NO. : 11/186429
DATED : January 6, 2009
INVENTOR(S) : Alan M. Todd et al.

It is certified that error appears in the above-identified patent and that said Letters Patent is hereby corrected as shown below:

On the cover page:

On the cover page, located in the References Cited under Other Publications, (right hand column, page 2), reference by Savage, delete the portion of text reading “Seeing* in a new light” and replace with --Seeing in a new light--.

In the claims:

Column 12, Claim 5, Lines 11-12, delete the portion of text reading “cavity and the second energy input supply ring” and replace with --cavity, and the second energy input supplying--.

Column 12, Claim 13, Line 45, delete the portion of text reading “prom the group” and replace with --from the group--.

Column 14, Claim 26, Line 30, delete the portion of text reading “coupling The” and replace with --coupling the--.

Column 14, Claim 30, Line 51, delete the portion of text reading “THZ seed” and replace with --THz seed--.

Signed and Sealed this

Seventeenth Day of March, 2009

JOHN DOLL
*Acting Director of the United States Patent and Trademark Office*